United States Patent [19]

Baran et al.

[11] 4,104,271

[45] Aug. 1, 1978

[54] 11β,18-EPOXY-9α-HALO-17,18-DIHYDROXY-3-OXO-17α-PREGN-4-ENE-21-CARBOXYLIC ACID γ-LACTONES AND CONGENERS

[75] Inventors: John S. Baran, Winnetka; Ivar Laos, Skokie, both of Ill.

[73] Assignee: G. D. Searle & Co., Chicago, Ill.

[21] Appl. No.: 806,024

[22] Filed: Jun. 13, 1977

[51] Int. Cl.² ............................................. C07J 17/00
[52] U.S. Cl. ................................................. 260/239.57
[58] Field of Search ................................... 260/239.57; /Machine Searched Steroids

[56] References Cited

U.S. PATENT DOCUMENTS

| | | | |
|---|---|---|---|
| 3,132,137 | 5/1964 | Clinton | 260/239.5 |
| 3,135,743 | 6/1964 | Clinton et al. | 260/239.57 |

*Primary Examiner*—Elbert L. Roberts
*Attorney, Agent, or Firm*—John M. Brown

[57] ABSTRACT

Preparation and the diuretic utility of 11β,18-epoxy-9α-halo-17,18-dihydroxy-3-oxo-17α-pregn-4-ene-21-carboxylic acid γ-lactones and congeners are disclosed.

4 Claims, No Drawings

11β,18-EPOXY-9α-HALO-17,18-DIHYDROXY-3-OXO-17α-PREGN-4-ENE-21-CARBOXYLIC ACID γ-LACTONES AND CONGENERS

This invention relates to 11β,18-epoxy-9α-halo-17,18-dihydroxy-3-oxo-17α-pregn-4-ene-21-carboxylic acid γ-lactones and congeners, and to processes for the preparation thereof. More particularly, this invention provides new, useful, and unobvious chemical compounds of the formula

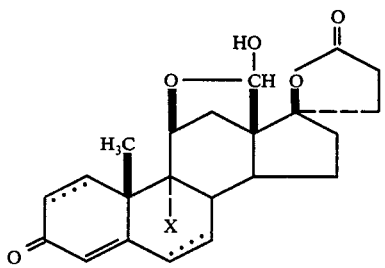

I wherein X represents halogen — preferably fluorine, chlorine, or bromine — and the dotted lines signify optional $\Delta^1$ and/or $\Delta^6$ unsaturation.

Those skilled in the art will recognize that the above-enformulated compounds, being lactols, can and do reversibly tautomerize to corresponding hydroxy aldehydes of the formula

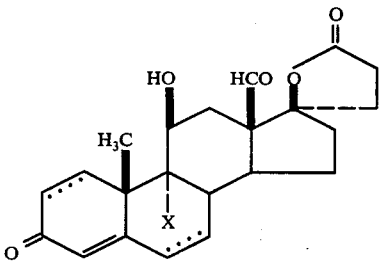

II wherein X and the dotted lines are defined as before. The proportions of the 2 tautomeric forms present in any given circumstance are dependent upon the physical state of the substance involved and its environment, i.e., whether it be liquid or solid and, if dissolved, in what solvent, at what temperature, and at what pH. Because tautomers cannot be readily represented by a single formula, embodiments of this invention are named and enformulated hereinafter exclusively as lactols for convenience only; both the lactol and hydroxy aldehyde forms are, nonetheless, within the ambit of the instant disclosure and claims.

The compounds to which this invention relates are useful by reason of their valuable biological properties. Thus, for example, they are diuretic: They reverse the renal electrolyte effects of mineralocorticoids such as desoxycorticosterone acetate (DCA) and d-aldosterone.

The capacity of the instant compounds to reverse the renal electrolyte effects of DCA can be demonstrated via the following test, substantially as described by C. M. Kagawa in chapter 34 of volume II of "Evaluation of Drug Activities: Pharmacometrics", edited by D. R. Laurence and A. L. Bacharach: A group (Group I) of 8 male Charles River rats, each weighing between 150 and 200 g, is adrenalectomized and maintained thereafter on sugar cubes and tap water ad libitum overnight. Each animal is thereupon subjected to these successive treatments: (a) 12 mg of DCA dissolved in 0.1 ml of corn oil is injected subcutaneously; (b) 2.4 mg of test compound dissolved or suspended in 0.5 ml of corn oil or other physiologically inert solvent (e.g., aqueous 0.9% sodium chloride) is administered subcutaneously or intragastrically; (c) 2.5 ml of aqueous 0.9% sodium chloride is injected subcutaneously. Urinary sodium and potassium are measured by customary techniques on samples of urine collected during the 4 hr immediately following treatment. Controls are provided by second and third groups of 16 and 8 150–200 g rats each, respectively, concurrently and identically treated excepting that in Group II, 0.33 mg of spironolactone is substituted for the test compound and the solution thereof is injected subcutaneously, while in Group III neither test compound nor spironolactone is administered. DCA produces sodium (Na) retention, loss of potassium (K), and a corresponding reduction in the mean log Na × 10/K. Spironolactone serves as an index of the validity of the test, the dose of 0.33 mg having been shown [Hoffmann et al., Arch. intern. pharmacodynamie, 165, 476 (1967)] to induce a 50% reversal of the effects of the DCA. Kagawa [Endocrinology, 74, 724 (1964)] reported a standard error of ±0.84 per 4-rat response, determined from a large number of tests and based on 60 degrees of freedom, for the mean log Na × 10/K measurement. From this it can be calculated that the least significant difference (P < 0.05) in mean log Na × 10/K between 2 groups of 8 rats each is ±0.168. It follows that when mean log Na × 10/K for Group I is equal to or greater than that for Group II, and the latter in turn exceeds the value for Group III by at least 0.168 log units, the reversals of the renal electrolyte effects of DCA represented thereby are significant. A compound active at the 2.4 mg dose level is retested at lower doses until the median effective dose (MED), a dose in mg sufficient to produce a 50% inhibition of the renal electrolyte effects of the DCA administered, can be calculated. The sucutaneous MED of 11β,18-epoxy-9α-fluoro-17,18-dihydroxy-3-oxo-17α-pregn-4-ene-21-carboxylic acid γ-lactone, the product of Example 1C hereinafter, was found to be 0.15 mg in the foregoing test.

When assayed for antimineralocorticoid activity in accordance with the procedure described by Hoffmann et al. in J. Pharmacol. Exp. Therap., 194, 450 (1975), using adrenalextomized male rats as the test animal and 0.2 μg of d-aldosterone as the mineralocorticoid, the intragastric potency of 11β,18-epoxy-9α-fluoro-17,18-dihydroxy-3-oxo-17α-pregna-1,4-diene-21-carboxylic acid γ-lactone, the product of Example 3C hereinafter, was found to be approximately 14% that of spironolactone.

The foregoing bioassay results are provided solely for illustrative purposes and, accordingly, should not be construed as either delimiting or exclusionary.

Preparation of the instant compounds can be accomplished by (1) contacting an 11β-hydroxy lactone of the formula

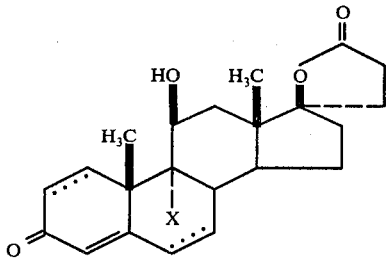

III with nitrosyl chloride in cold pyridine to produce an 11β-nitrosyl compound of the formula

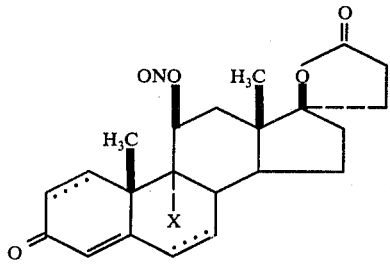

IV (2) irradiating a compound of Formula IV, using a mercury arc as the light source and a filter (for example, Pyrex glass) to screen out wave lengths below 300 nanometers, thereby producing an 11β-hydroxy-18-(hydroxyimino) lactone of the formula

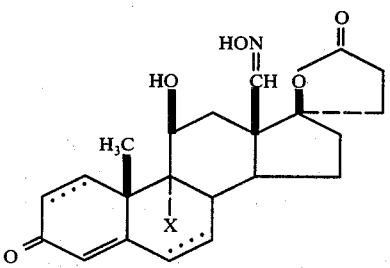

V and (3) contacting a compound of Formula V with sodium nitrite in acetic acid. Inasmuch as the nitroso compounds of Formula IV tend to hydrolyze on standing, especially in a solvent medium, it is preferred to convert them promptly to the oximes of Formula V. X and the dotted lines in Formulas III-V retain the meanings originally assigned.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the disclosure, temperatures are given in degrees centigrade and relative amounts of materials in parts by weight, except as otherwise noted.

EXAMPLE 1

A. To a solution of 12 parts of 9α-fluoro-11β,17-dihydroxy-3-oxo-17α-pregn-4-ene-21-carboxylic acid γ-lactone (U.S. Pat. No. 2,925,416) in 50 parts of pyridine at approximately −10° is added, with stirring, a solution of 5 parts of nitroso chloride in 50 parts of pyridine. Stirring is continued for 20 minutes after the addition is complete, whereupon the resultant solution is stirred into 1000 parts of a 50:50 mixture of ice and water. The crystalline precipitate which forms is isolated by filtration, washed on the filter with water, and dried in vacuo at room temperature. The product is 9α-fluoro-17-hydroxy-11β-nitroso-3-oxo-17α-pregn-4-ene-21-carboxylic acid γ-lactone, having the formula

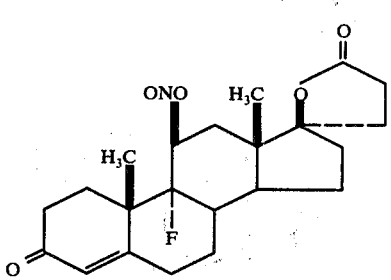

B. A solution of 5 parts of 9α-fluoro-17-hydroxy-11β-nitroso-3-oxo-17α-pregn-4-ene-21-carboxylic acid γ-lactone in 900 parts of methylbenzene under nitrogen is irradiated at 20° for approximately ½ hour with Pyrex-filtered light from a 450-watt mercury arc, whereupon the reaction mixture is stripped of solvent by vacuum distillation. The residue is washed by trituration with 1,1'-oxybisethane and dried in vacuo. The crystalline product thus isolated is 9α-fluoro-11β,17-dihydroxy-18-(hydroxyimino)- 3-oxo-17α-pregn-4-ene-21-carboxylic acid γ-lactone. It has the formula

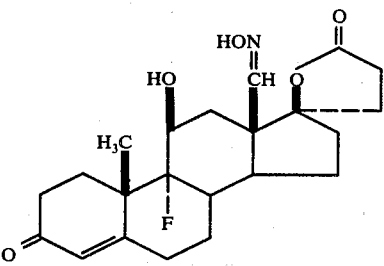

C. To a solution of 2 parts of 9α-fluoro-11β,17-dihydroxy-18-(hydroxyimino)-3-oxo-17α-pregn-4-ene-21-carboxylic acid γ-lactone in 40 parts of acetic acid is added, with stirring, 13 parts of aqueous 5% sodium nitrite. The resultant mixture is stirred for 10 minutes, then extracted with chloroform. The chloroform extract is consecutively washed with water and a saturated aqueous solution of sodium sulfate, whereupon solvent is removed by vacuum distillation. The residue is taken up in a 20% solution of ethyl acetate in benzene; and the resultant solution is chromatographed on silicic acid, using 20%, 30%, and 40% solutions of ethyl acetate in benzene as developing solvents. Eluates comprising 40% ethyl acetate in benzene are combined, whereupon solvents are removed by vacuum distillation and the residue recrystallized from a mixture of 2-oxopropane and hexane. The product is 11β,18-epoxy-9α-fluoro-17,18-dihydroxy-3-oxo-17αpregn-4-ene-21-carboxylic acid γ-lactone melting at 247°-250°, and having the formula

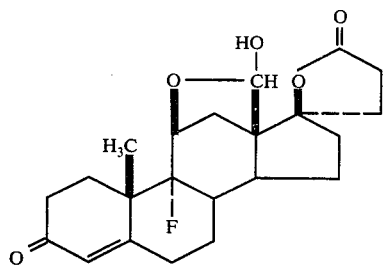

EXAMPLE 2

A. Substitution of 12 parts of 9α-bromo-11β,17-dihydroxy-3-oxo-17α-pregn-4-ene-21-carboxylic acid γ-lactone (U.S. Pat. No. 2,925,416) for the 9α-fluoro-11β,17-dihydroxy-3-oxo-17α-pregn-4-ene-21-carboxylic acid γ-lactone called for in Example 1A affords, by the procedure there detailed, 9α-bromo-17-hydroxy-11β-nitroso-3-oxo-17α-pregn-4-ene-21-carboxylic acid γ-lactone.

B. Substitution of 5 parts of 9α-bromo-17-hydroxy-11β-nitroso-3-oxo-17α-pregn-4-ene-21-carboxylic acid γ-lactone for the 9α-fluoro-17-hydroxy-11β-nitroso-3-oxo-17α-pregn-4-ene-21-carboxylic acid γ-lactone called for in Example 1B affords, by the procedure there detailed, 9α-bromo-11β,17-dihydroxy-18-(hydroxyimino)-3-oxo-17α-pregn-4-ene-21-carboxylic acid γ-lactone.

C. To a solution of 2 parts of 9α-bromo-11β,17-dihydroxy-18-(hydroxyimino)-3-oxo-17α-pregn-4-ene-21-carboxylic acid γ-lactone in 40 parts of acetic acid is added, with stirring, 13 parts of aqueous 5% sodium nitrite. The resultant mixture is stirred for 10 minutes, then extracted with chloroform. The chloroform extract is consecutively washed with water and a saturated aqueous solution of sodium sulfate, whereupon solvent is removed by vacuum distillation. The residue is taken up in a 20% solution of ethyl acetate in benzene; and the resultant solution is chromatographed on silicic acid, using 20%, 30%, and 40% solutions of ethyl acetate in benzene as developing solvents. Eluates comprising 40% ethyl acetate in benzene are combined, whereupon solvents are removed by vacuum distillation. The residue, which can be further purified by recrystallization from a mixture of 2-oxopropane and hexane, is 9α-bromo-11β,18-epoxy-17,18-dihydroxy-3-oxo-17α-pregn-4-ene-21-carboxylic acid γ-lactone having the formula

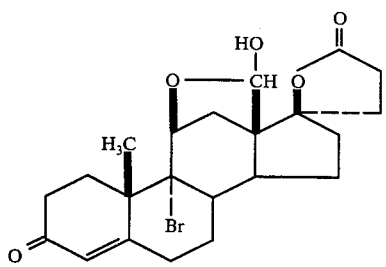

EXAMPLE 3

A. Substitution of 12 parts of 9α-fluoro-11β,17-dihydroxy-3-oxo-17α-pregna-1,4-diene-21-carboxylic acid γ-lactone (U.S. Pat. No. 3,053,840) for the 9α-fluoro-11β,17-dihydroxy-3-oxo-17α-pregn-4-ene-21-carboxylic acid γ-lactone called for in Example 1A affords, by the procedure there detailed, 9α-fluoro-17-hydroxy-11β-nitroso-3-oxo-17α-pregna-1,4-diene-21-carboxylic acid γ-lactone.

B. Substitution of 5 parts of 9α-fluoro-17-hydroxy-11β-nitroso-3-oxo-17α-pregna-1,4-diene-21-carboxylic acid γ-lactone for the 9α-fluoro-17-hydroxy-11β-nitroso-3-oxo-17α-pregn-4-ene-21-carboxylic acid γ-lactone called for in Example 1B affords, by the procedure there detailed, 9α-fluoro-11β,17-dihydroxy-18-(hydroxyimino)-3-oxo-17α-pregna-1,4-diene-21-carboxylic acid γ-lactone.

C. Substitution of 2 parts of 9α-fluoro-11β,17-dihydroxy-18-(hydroxyimino)-3-oxo-17α-pregna-1,4-diene-21-carboxylic acid γ-lactone for the 9α-fluoro-11β,17-dihydroxy-18-(hydroxyimino)-3-oxo-17α-pregn-4-ene-21-carboxylic acid γ-lactone called for in Example 1B affords, by the procedure there detailed, 11β,18-epoxy-9α-fluoro-17,18-dihydroxy-3-oxo-17α-pregna-1,4-diene-21-carboxylic acid γ-lactone melting at 240°–242°, and having the formula

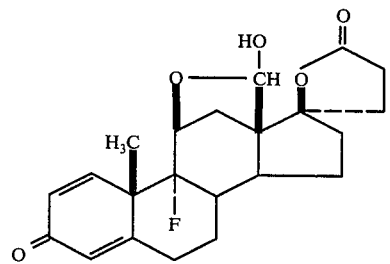

EXAMPLE 4

A. Substitution of 12 parts of 9α-fluoro-11β,17-dihydroxy-3-oxo-17α-pregna-4,6-diene-21-carboxylic acid γ-lactone (U.S. Pat. No. 3,053,840) for the 9α-fluoro-11α,17-dihydroxy-3-oxo-17α-pregn-4-ene-21-carboxylic acid γ-lactone called for in Example 1A affords, by the procedure there detailed, 9α-fluoro-17-hydroxy-11β-nitroso3-oxo-17α-pregna-4,6-diene-21-carboxylic acid γ-lactone.

B. Substitution of 5 parts of 9α-fluoro-17-hydroxy-11β-nitroso-3-oxo-17α-pregna-4,6-diene-21-carboxylic acid γ-lactone for the 9α-fluoro-17-hydroxy-11β-nitroso-3-oxo-17α-pregn-4-ene-21-carboxylic acid γ-lactone called for in Example 1B affords, by the procedure there detailed, 9α-fluoro-11β,17-dihydroxy-18-(hydroxyimino)-3-oxo-17α-pregna-4,6-diene.

C. Substitution of 2 parts of 9α-fluoro-11β,17-dihydroxy-18-(hydroxyimino)-3-oxo-17α-pregna-4,6-diene-21-carboxylic acid γ-lactone for the 9α-bromo-11β,17-dihydroxy-18-(hydroxyimino)-3-oxo-17α-pregn-4-ene-21-carboxylic acid γ-lactone called for in Example 2C affords, by the procedure there detailed, 11β,18-epoxy-9α-fluoro-17,18-dihydroxy-3-oxo-17α-pregna-4,6-diene-21-carboxylic acid γ-lactone, having the formula

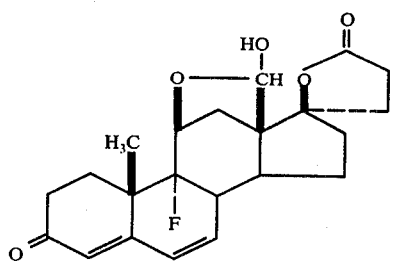

EXAMPLE 5

A. Substitution of 12 parts of 9α-fluoro-11β,17-dihydroxy-3-oxo-17α-pregna-1,4,6-triene-21-carboxylic acid γ-lactone (U.S. Pat. No. 3,053,840) for the 9α-fluoro-11β,17-dihydroxy-3-oxo-17α-pregn-4-ene-21-carboxylic acid γ-lactone called for in Example 1A affords, by the procedure there detailed, 9α-fluoro-17-hydroxy-11β-nitroso-3-oxo-17α-pregna-1,4,6-triene-21-carboxylic acid γ-lactone.

B. Substitution of 5 parts of 9α-fluoro-17-hydroxy-11β-nitroso-3-oxo-17α-pregna-1,4,6-triene-21-carboxylic acid γ-lactone for the 9α-fluoro-17-hydroxy-11β-nitroso-3-oxo-17α-pregn-4-ene-21-carboxylic acid γ-lactone called for in Example 1B affords, by the procedure there detailed, 9α-fluoro-11β,17-dihydroxy-18-(hydroxyimino)-3-oxo-17α-pregna-1,4,6-triene-21-carboxylic acid γ-lactone.

C. Substitution of 2 parts of 9α-fluoro-11β,17-dihydroxy-18-(hydroxyimino)-3-oxo-17α-pregna-1,4,6-triene-21-carboxylic acid γ-lactone for the 9α-bromo-11β,17-dihydroxy-18-(hydroxyimino)-3-oxo-17α-pregn-4-ene-21-carboxylic acid γ-lactone called for in Example 2C affords, by the procedure there detailed, 11β,18-epoxy-9α-fluoro-17,18-dihydroxy-3-oxo-17α-pregna-1,4,6-triene-21-carboxylic acid γ-lactone, having the formula

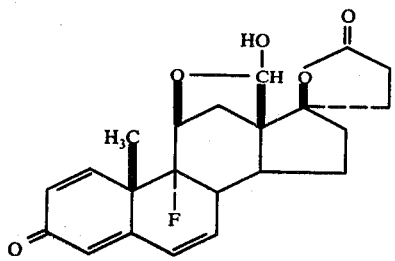

What is claimed is:
1. A compound of the formula

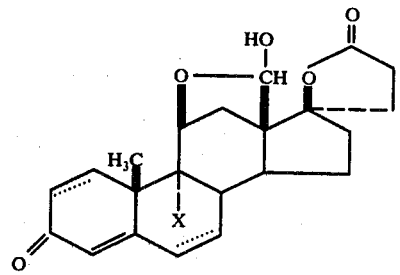

wherein X represents fluorine, chlorine, or bromine and the dotted lines signify optional Δ¹ and/or Δ⁶ unsaturation.

2. A compound according to claim 1 having the formula

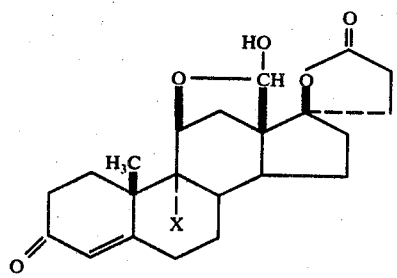

wherein X represents fluorine, chlorine, or bromine.

3. A compound according to claim 1 which is 11β,18-epoxy-9α-fluoro-17,18-dihydroxy-3-oxo-17α-pregn-4-ene-21-carboxylic acid γ-lactone.

4. A compound according to claim 1 which is 11β,18-epoxy-9α-fluoro-17,18-dihydroxy-3-oxo-17α-pregna-1,4-diene-21-carboxylic acid γ-lactone.

* * * * *